United States Patent [19]
McHaney et al.

[11] Patent Number: 5,827,327
[45] Date of Patent: Oct. 27, 1998

[54] CARBON CONTAINING VASCULAR GRAFT AND METHOD OF MAKING SAME

[75] Inventors: James M. McHaney, Chandler; Christopher E. Banas, Mesa, both of Ariz.

[73] Assignee: IMPRA, Inc., Tempe, Ariz.

[21] Appl. No.: 777,006

[22] Filed: Jan. 3, 1997

Related U.S. Application Data

[63] Continuation of Ser. No. 311,497, Sep. 23, 1994, abandoned.

[51] Int. Cl.$^6$ ..................................................... A61F 2/06
[52] U.S. Cl. ................................................................ 623/1
[58] Field of Search ................................. 623/1, 11, 12

[56] References Cited

U.S. PATENT DOCUMENTS

| | | |
|---|---|---|
| 2,782,180 | 2/1957 | Weidman . |
| 3,473,087 | 10/1969 | Slade ............................................ 317/2 |
| 3,512,183 | 5/1970 | Sharp . |
| 3,585,647 | 6/1971 | Gajewski et al. . |
| 3,609,768 | 10/1971 | Avres . |
| 3,845,186 | 10/1974 | Shaw ...................................... 264/104 |
| 3,914,802 | 10/1975 | Reick . |
| 3,953,566 | 4/1976 | Gore . |
| 3,962,153 | 6/1976 | Gore . |
| 3,971,670 | 7/1976 | Homsy .................................. 156/196 |
| 3,992,725 | 11/1976 | Homsy ............................................ 3/1 |
| 4,118,532 | 10/1978 | Homsy .................................. 428/294 |
| 4,127,902 | 12/1978 | Homsy ............................................ 3/1 |
| 4,129,470 | 12/1978 | Homsy .................................. 156/155 |
| 4,156,127 | 5/1979 | Sako et al. .............................. 219/301 |
| 4,209,480 | 6/1980 | Homsey . |
| 4,229,838 | 10/1980 | Mano ......................................... 3/1.4 |
| 4,321,711 | 3/1982 | Mano ......................................... 3/1.4 |
| 4,455,690 | 6/1984 | Homsy ............................................ 3/1 |
| 4,537,791 | 8/1985 | Tarjan ........................................ 427/2 |
| 4,563,485 | 1/1986 | Fox, Jr. et al. ......................... 523/113 |
| 4,576,608 | 3/1986 | Homsy ...................................... 623/11 |
| 4,718,907 | 1/1988 | Karwoski et al. ....................... 623/12 |
| 4,749,585 | 6/1988 | Greco et al. ................................ 427/2 |
| 4,816,339 | 3/1989 | Tu et al. ................................. 428/421 |
| 4,822,355 | 4/1989 | Bhuvaneshwar ........................... 623/2 |
| 4,888,245 | 12/1989 | Witzko .................................... 428/421 |
| 5,084,151 | 1/1992 | Vallana et al. ..................... 204/192.11 |
| 5,133,845 | 7/1992 | Vallana et al. ..................... 204/192.11 |
| 5,181,903 | 1/1993 | Vann et al. ................................ 600/36 |
| 5,192,310 | 3/1993 | Herweck et al. ........................... 623/1 |
| 5,213,580 | 5/1993 | Slepian et al. ............................. 623/1 |
| 5,380,594 | 1/1995 | Von Blücher et al. ................. 428/403 |

FOREIGN PATENT DOCUMENTS

| | | |
|---|---|---|
| 857934 | 12/1977 | Belgium . |
| 0 661 094 A3 | 9/1995 | European Pat. Off. ......... B01J 20/28 |
| 225574-35 | of 1973 | Germany . |
| 1589885 | of 1964 | U.S.S.R. . |

OTHER PUBLICATIONS

"Modified Polytetrafluoroethylene: Indium 111–labeled platelet deposition on carbon–lined and high porosity polytetrafluoroethylene grafts" by Tsuchida, H., Cameron, B.L., Marcus, C.S. and S.E. Wilson;, *Journal of Vascular Surgery*, vol. 16, No. 4: pp. 643–650 (1992).

"A Small Arterial Substitute: Expanded Microporous Polytetrafluoroethylene: Patency Versus Porosity" by Campbell, et al., *Annals of Surgery*, vol. 182, No. 2, pp. 138–143, submitted for publication Mar. 24, 1975.

"Small Vessel Replacement With Gore–Tex (Expanded Polytetrafluoroethylene)" by Florian, et al., *Arch Surgery*, vol. 111, pp. 267–270 (Mar. 1976).

"Graphite–Expanded Polytetrafluoroethylene: An Improved Small Artery Prosthesis" by Goldfarb, et al., *Trans.Am.Soc.Artif.Intern.Organ*, vol. XXIII, pp. 268–276 (1977).

(List continued on next page.)

*Primary Examiner*—Michael J. Milano
*Attorney, Agent, or Firm*—David G. Rosenbaum

[57] ABSTRACT

A carbon containing vascular graft formed of expanded polytetrafluoroethylene and activated carbon admixed with at least a portion of the expanded polytetrafluoroethylene. A bioactive substance may be incorporated in the carbon containing vascular graft.

16 Claims, 6 Drawing Sheets

OTHER PUBLICATIONS

"Modified Graphite–Expanded PTFE (G–PTFE) For Use as a Superior Vena Cava (SVC) Substitute" by D. Goldfarb, J. Houk, J. Moore, Sr., and W. Catron, *Trans.Am.Soc.Artif.Intern.Organs*, vol. 24, pp. 201–207.

"Present Status of Carbon Grafts" by William V. Sharp, pp. 326–330.

"Update on Carbon–Coated Grafts" by William V. Sharp, *Modern Vascular Grafts*, pp. 215–224.

"Pyrolytic Carbon–Coated Vascular Prostheses" by Stewart S. Scott, M.D., Lee R. Gaddy, B.A., and S. Para, M.S., *Journal of Surgical Research*, vol. 29, pp. 395–405 (1980).

"Carbon Fiber–Reinforced Carbon as a Potential Implant Material" by D. Adams, D.F. Williams, *Journal of Biomedical Materials Research*, vol. 12, pp. 35–42, (1978).

"Heparin application to graphite–coated intravascular protheses", by James D. Whiffen, M.D., Robert Dutton, B.S., William P. Young, M.D., Vincent L. Gott, M.D., *Surgery*, vol. 56, No. 2, pp. 404–412 (Aug. 1964).

"ULTI Carbon Gortex: A New Vascular Graft", by Robert Debski, M.D., Harvey Borovetz, Ph.D., Axel Haubold, Ph.D., and Robert Hardesty, M.D., *Current Surgery*, pp. 198–200 (May–Jun. 1983).

"Endothelial Cell Seeding of ULTI Carbon–coated Small–diameter PTFE Vascular Grafts", by Kevin L. Boyd, Steven P. Schmidt, Todd R. Pippert, and William V. Sharp, *Trans.Am.Artif.Intern.Organs.*, pp. 631–635, (1987).

"Polytetrafluoroethylene Grafts Coated with ULTI Carbon" by R. Debski, H. Borovetz, A. Haubold, and R. Hardesty, *Trans.Am.Soc.Artif.Intern Organs*, vol. 28, pp. 456458, (1982).

"Pyrolytic Carbon–Coated Grafts", by William V. Sharp, M.D. and Phillip C. Teague, pp. 203–213.

"The coating of intravascular plastic prostheses with colloidal graphite", by Vincent I. Gott, M.D., Donald E. Koepke, M.D., Ronald L. Daggett, B.S., M.S.M.E., William Zarnstorff, B.S.E.E., and William P. Young, M.D., *Surgery*, vol. 50, No. 2, (Aug. 1961).

"Carbon Transcutaneous Access Device (CTAD)" by A.L. Golding, A.R. Nissenson, R. Higgins, and D. Raible, *Trans.Am.Soc.Artf.Intern.Organs*, vol. 26, pp. 105–110, (1980).

"Blood Access Without Skin Puncture", by A.J. Collins, F.L. Shapiro, P. Keshaviah, K. Ilstrup, R. Anderson, T. O'Brien, F.J. Martinez, and L.C. Cosentino, *Trans.Am.Soc.Artf.Intern.Organs*, vol. 27, pp. 308–313, (1981).

"Expanded PTFE: Long–Term Follow–up", by W. Catron, D. Goldfarb, J. Moore, J. Houk, and K. Jeffery, *Trans.Am..Soc.Artf.Intern.Organs*, vol. 28, pp. 190–194, (1982).

"Studies on the Porous Polytetrafluoroethylene as The Vascular Prothesis" by Matsumoto, et al., *Artificial Organs*, vol. 1, No. 1, pp. 44–47 (1972).

"Experimental Studies on the Expanded Polytetrafluoroethylene as The Vascular Prosthesis—The Second Report: Its Applicability to Vein" by Matsumoto, et al., *Artifical Organs*, Supplement, pp. 15–17 (1973).

"Studies on Expanded Polytetrafluoroethylene as The Vascular Prosthesis (The Third Report): Its Antithrombogencity, Surface Properties and Porosity" by Matsumoto, et al., *Artificial Organs*, vol. 2, No. 5, pp. 337–341 (1974).

"Application of Expanded Polytetrafluoroethylene to Vascular Prosthesis (The 4th Report): Comparison Between Expanded Polytetrafluoroethylene and Polytetrafluoroethylene–methylmetracrylate Graftcopolymer Implanted into the Portal Vein" by Matsumoto, et al., *Artificial Organ*, vol. 3 Supplement published Sep. 30, 1974.

"Application of Expanded Polytetrafluoroethylene to Vascular Prosthesis—Application to the Portal Vein System, and Pore and Pseudo–intima" by Kimura, Matsumoto, et al., *Artificial Organs*, vol. 5, No. 2, pp. 85–89 (1976).

"Experimental Studies of Gore–Tex Graft for Replacement of the Vena Cave—Effect of Anticoagulants" by Fujiwara, et al., *Artificial Organs*, vol. 5, No. 2, pp. 105–111 (1976).

"A New Venous Prosthesis" by Soyer, Lempinen, Cooper, et al., *Surgery*, vol. 72, No. 6, pp. 864–872 (1972).

"Replacement of Portal Vein During Pancreatectomy for Carcinoma" by Norton and Eiseman, *Surgery*, vol. 77, No. 2, pp. 280–284 (Feb. 1975).

Junkosha Japanese Patent Publication No. 22792/74 filed Jun. 22, 1972, published Feb. 28, 1974.

"A–V Shunts Created in New Ways", by Volder, et al., *Trans ASAIO*, vol. XIX, pp. 38–42 (1973).

"Induced Growth of Connective Tissue in Cardiovascular Prosthesis" by Volder, et al., *Trans ASAIO*, vol. XX, pp. 521–529 (1974).

"Use of Goretex Grafts for Replacement of the Superior and Inferior Venae Cavae" by Fujiwara, et al., *The Journal of Thoracic and Cardiovascular Surgery*, vol. 67, No. 5, pp. 774–779 (May 1974).

"Expanded Polytetrafluoroethylene (PTFE)—A Superior Biocompatible Material for Vascular Prostheses" by Goldfarb, et al., *Proc. San Diego Biomed. Symp.* vol. 14:451 (Jan./Feb. 1975).

Fig-13

CARBON CONTAINING VASCULAR GRAFT AND METHOD OF MAKING SAME

This is a continuation of application Ser. No. 08/311,497 filed on Sep. 23, 1994, now abandoned.

BACKGROUND OF THE INVENTION

The present invention relates generally to vascular grafts. More particularly, the present invention relates to a carbon lined vascular graft which results from co-extruding a carbon component and a polymer component to form a tubular graft which comprises carbon as an integral part of the wall of the tubular graft. The present invention further relates to a carbon/polymer graft having a time releasable bioactive substance incorporated within the carbon and a method for making the carbon/polymer graft containing the bioactive substance.

Early studies of the electrochemistry occurring at the blood synthetic interface of synthetic grafts and in normal blood vessels established that the inner surface of blood vessels are electronegative when compared with their outer surfaces. This evidence prompted the theory that a negative surface charge prevents thrombosis while a positive surface charge promotes it. Carbon is a versatile element which has been added to various vascular synthetics to promote electrical conductivity. The electronegative charge of carbon was found to act as a thrombosis deterrent when used to coat the surfaces of grafts.

In addition, various forms of carbon have been shown to have a high degree of biocompatability. Two specific forms of carbon, namely vitreous carbon and turbostratic carbon, have drawn great interest in the field of biological implantations. Vitreous carbons comprise a loose lattice configuration resulting from the thermal degradation of organic materials. In contrast, turbostratic carbons comprise an orderly lattice arrangement which is formed by a heat process under pressure.

A vascular graft having a turbostratic carbon layer comprising pyrolitic carbon is prepared by a chemical vapor-deposition process which utilizes a vacuum apparatus for carbon sputtering. This process has been disclosed in detail in the prior art. Examples of this disclosure are evident in U.S. Pat. Nos. 4,537,791, 5,084,151 and 5,133,845. Three particular pyrolytic carbons are defined by the temperature at which they are deposited. High-temperature isotropic carbon (HTI) is produced at temperatures greater than 2000° C., low-temperature isotropic carbon (LTI) is deposited at temperatures less than 1500° C., and ultra-low-temperature isotropic carbon (ULTI) is deposited at temperatures less than 100° C. of these temperature defined pyrolytic carbons, the use of ULTI is preferred because it can be applied to heat-sensitive fabrics and polymers.

Carbon has also been incorporated into vascular prostheses by coating the vascular prostheses with colloidal graphite. More specifically, an anticoagulant, such as heparin is mixed with the prosthesis material, typically a flexible polymeric resin, and toluene or other aromatic solvent, and further combined with graphite to form a luminal layer of the vascular prosthesis. The graphite functions as an adsorbent to hold the anticoagulant. After treating the vascular prosthesis with toluene, the above-described graphite coating is poured into the vascular prosthesis, allowed to remain in contact with the luminal surface of the prosthesis, and then drained from the prothesis. The remaining coating on the luminal surface of the prosthesis is air dried and then cured to the prosthesis with heat. An example of such a method is described in U.S. Pat. Nos. 3,585,647. Such carbon coated vascular grafts are also disclosed and evaluated in several scientific journal articles. Gott, V. L., Whiffen, J. D., Dutton, R. C., "Heparin bonding on colloidal graphite surfaces." *Science,* 142:1297, 1963.; Whiffen, J. D., Dutton, R., Young, W. P., Gott, V. L., "Heparin application to graphite coated intravascular prostheses." *Surgery,* 56(2):404, 1964.; Gott, V. L., Whiffen, J. D., Koepke, D. E., Daggett, R. L., Beake, W. C., Young, W. P., "Techniques of applying a graphite-benzalkonium-heparin coating to various plastics and metals." *Transactions American Society of Artificial Internal Organs,* 10:213, 1964.

Studies of carbon coated vascular grafts, as described above, have shown similar results. These results include the finding that the carbon coated grafts exhibit reduced thrombogenicity and improved patency over non carbon coated grafts.

Nevertheless, none of the foregoing carbon coated grafts form an integral part of the wall of the graft. Consequently, the previously described vascular grafts exhibit certain undesirable characteristics when compared to a graft which is impregnated with a carbon element during the production of the graft. The high probability of carbon leaching into the tissues surrounding the graft is one such characteristic. Furthermore, those previously described carbon coated grafts may not exhibit the same wall thickness, density, pore size, suture retention strength, and tensile strength as their non-coated counterparts.

Accordingly, there is a need for a method to produce a vascular graft having carbon as an integral part of the wall of the graft in order to provide a vascular graft which exhibits a less thrombogenic blood contact surface with a minimal amount of carbon leaching. Such a graft should also exhibit continuity in wall thickness, density, pore size, suture retention strength, and tensile strength throughout the structure of the graft. Furthermore, the electronegative charge of the carbon component contained within such a carbon containing graft may facilitate the binding of a time releasable bioactive substance, such as an anticoagulant or antimicrobial agent, to the graft.

SUMMARY OF THE INVENTION

It is a principal object of the present invention to provide a method for making a vascular graft which exhibits reduced thrombogenicity and increased patency.

It is a further object of the present invention to provide a method for making a carbon containing vascular graft wherein the carbon component of the graft forms an integral portion of the luminal wall of the graft.

It is still a further object of the present invention to provide a method for making a carbon containing vascular graft which exhibits a minimal amount of carbon leaching from the wall of the graft into the tissue surrounding the graft.

It is yet a further object of the present invention to provide a method for making a carbon containing vascular graft which maintains continuity in wall thickness, density, pore size, suture retention strength, and tensile strength throughout the structure of the graft.

It is still a further object of the present invention to provide a method for making a carbon containing vascular graft which exhibits the desirable properties of expanded polytetrafluoroethylene (PTFE) with a less thrombogenic blood contact surface.

It is still a further object of the present invention to provide a method for making a carbon-lined vascular graft wherein the carbon component of the graft forms an integral portion of the luminal wall of the graft or, alternatively, an integral portion of the outer wall of the graft.

It is yet a further object of the present invention to provide a method for making a carbon-lined vascular graft, having a polymer/carbon tubular extrudate and a polymer tubular extrudate, which exhibits substantially uniform porosity throughout the thickness of the graft's wall such that the carbon containing layer of the graft has a porosity similar to the polymer layer of the graft.

It is still a further object of the present invention to provide a carbon containing vascular graft having a time releasable bioactive substance loaded into the graft and a method for making the bioactive loaded carbon containing graft.

According to a broad aspect of the invention, there is provided a method for making a carbon containing vascular graft, which is comprised primarily of polymers or a polymeric material, which includes the following steps: 1) molding a preform billet of material from a preform barrel wherein the preform tube of material contains an inner cylinder comprising a polymer compound or a polymeric carbon compound and an outer cylinder comprising a polymer compound or a polymeric carbon compound such that the outer cylinder surrounds the inner cylinder, 2) extruding the preform billet of material through a die to form a tubular extrudate, 3) expanding the tubular extrudate, and 4) sintering the expanded tubular extrudate.

The polymeric compound is comprised from a polymer resin, preferably a polytetrafluoroethylene (PTFE) resin, and a suitable lubricant such as mineral spirits. The polymeric carbon compound is comprised from a polymer resin, preferably a PTFE resin, a carbon element, such as activated charcoal powder or graphite with activated charcoal powder, and a suitable lubricant such as mineral spirits. The polymer element contained in the polymer compound is preferably the same as the polymer element contained in the polymeric carbon compound.

In order to form the preform billet, the preform barrel in step 1 is divided into two hollow concentrical cylindrical sections. This configuration is accomplished by placing a first hollow tube within a second hollow tube having a greater diameter than the first hollow tube. A polymer resin and lubricant are combined to form the polymer compound and a polymer resin, lubricant, and carbon component are combined to form the polymeric carbon compound. Compounding is achieved by alternately sifting, shaking, and incubating the combined components which make up the respective compounds.

If an intraluminal carbon lined vascular graft is desired, the polymeric carbon compound is poured into the hollow inner cylinder and the polymeric compound is poured into the hollow outer cylinder. The preform barrel is compressed to compact the respective compounds and then removed. The resulting structure is a polymeric preform billet having a carbon component comprising an inner cylindrical section of the billet. As discussed above, this preform billet is then extruded, expanded, and sintered to form a hollow polymeric tubular vascular graft which has a carbon component forming an integral part of its luminal wall.

Alternatively, if an exterior or outer carbon lined vascular graft is desired, the polymeric compound is poured into the hollow inner cylinder and the polymeric carbon compound is poured into the hollow outer cylinder. Compression of the preform barrel, compaction of the respective compounds to form a dual compound billet, extrusion of the preform billet, and expansion and sintering of the resulting tubular vascular graft are then performed as described above. The resulting product is a hollow polymeric tubular vascular graft having an outer carbon layer which forms an integral part of the outer wall of the vascular graft.

The above described method for co-extruding a dual compound billet may also be carried out after placing the carbon polymeric compound in both the inner and outer hollow cylinder sections of the preform barrel. The process will then produce a carbon containing polymeric tubular vascular graft having uniform carbon polymeric material throughout the wall of the graft. Alternatively, carbon polymeric compounds having different percent weights of their carbon component may be loaded into the inner and outer cylindrical sections, respectively, to produce a vascular graft having two co-extruded carbon layers of differing carbon percentages.

A uniform polymeric carbon compound may also be loaded into an undivided preform barrel to form a single billet having a uniform carbon composition throughout the billet. The billet may then be extruded to form a vascular graft having a uniform carbon polymeric material throughout the wall of the graft.

Preformers having more than one divider may also be used as part of the inventive method to form billets having multiple layers (e.g. three, four, etc.) which can then be co-extruded to form grafts having multiple layers of varying compounds wherein at least one of the layers comprises a carbon containing compound.

There is also provided a carbon containing vascular graft comprising a carbon component and a polymer component, which form an integral carbon and polymer wall structure, wherein the vascular graft contains a bioactive substance which is capable of being time released from the vascular graft.

The objectives, features, and advantages of the present invention will become more apparent to those skilled in the art from the following more detailed description of the preferred embodiment of the invention made in conjunction with the accompanying drawings.

DETAILED DESCRIPTION OF THE PREFERRED EMBODIMENTS

Figures 1, 3:
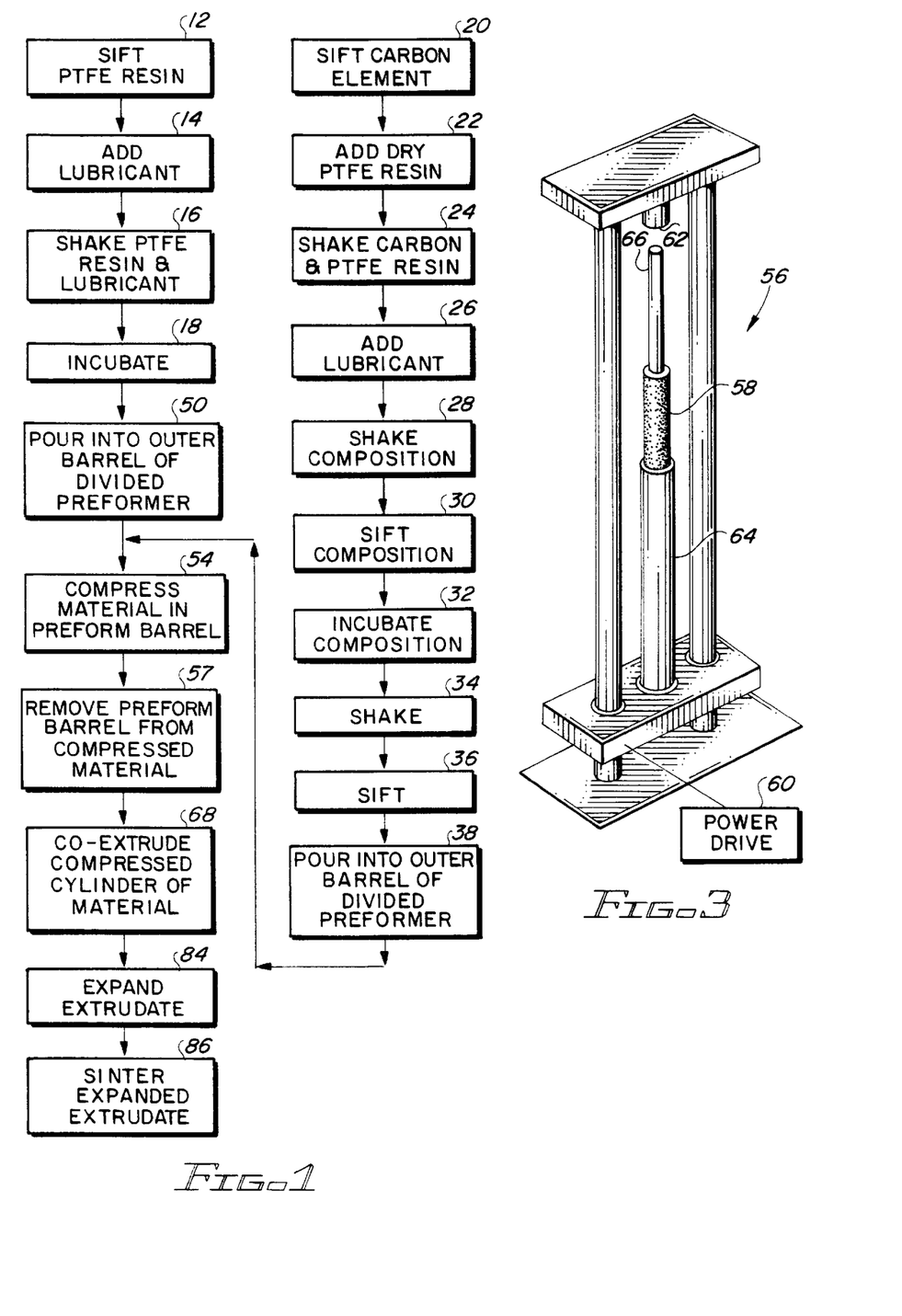
FIG. 1 is a diagrammatic representation of the preferred method for making an intraluminal carbon lined vascular graft.
FIG. 3 is a perspective view of the press which is used to compact the composition contained within the preform barrel during the inventive process.

A flowchart depicting the inventive process 10 for making an intraluminal carbon lined vascular graft is shown in FIG. 1. The first four steps define the compounding of a polymeric compound. PTFE resin is first sifted 12. A suitable amount of lubricant, such as mineral spirits, is added 14 to enable the PTFE to flow easily through extrusion equipment. The combined PTFE resin and lubricant are then placed in a shaker device and shaken 16 so that the lubricant coats and penetrates each of the PTFE resin particles. The thoroughly mixed combination of PTFE resin and lubricant is then incubated 18 in a warming cabinet overnight which is maintained at a temperature of approximately 85° F. The incubation period allows for a further and more equal dispersion of the lubricant throughout the PTFE resin. The incubation step concludes the inventor's best mode for efficiently and effectively compounding the polymeric compound which comprises part of the inventive process. However, further mixing and heating steps may be undertaken during the compounding process.

Next, the compounding of a polymeric carbon compound is performed by first sifting a carbon element 20, such as activated charcoal powder or graphite with activated charcoal powder, through a number four-hundred (#400) sieve using a mechanical sieve shaker. An amount of dry PTFE resin is then measured and added 22 to the carbon element. This step is preferably performed in a cold room. The carbon and PTFE resin combination is shaken 24 in a cold storage room for approximately three minutes. The carbon and PTFE resin combination is then passed back into the cold room, and a lubricant is added 26 to the composition. The resulting combination (carbon + PTFE resin + lubricant) is shaken 28 and then sifted 30 through a number twenty (#20) sieve.

The combination is then incubated 32 overnight in a warming cabinet which is maintained at a temperature of approximately 85° F., and removed from the incubator at least twenty minutes prior to preforming the mixture which is described subsequently. The combination is then shaken 34 and subsequently sifted 36 through a number twenty (#20) sieve.

EXAMPLE 1

The following amounts were used in compounding the polymeric carbon compound and the polymeric compound as outlined in FIG. 1.

Polymeric carbon compound:

| PTFE resin | 230 grams |
| carbon (activated charcoal powder) | 20 grams |

The activated carbon had a particle size wherein 97% of the activated carbon passed through a 150 micron sieve. "NORIT" activated carbon and "MALLINCKRODT" activated carbon both meet this specification.

Polymeric compound:

| PTFE resin | 250 grams |

The carbon component of the polymeric carbon compound is preferably 3% to 20% by weight of the PTFE resin.

Figures 2, 4, 5:
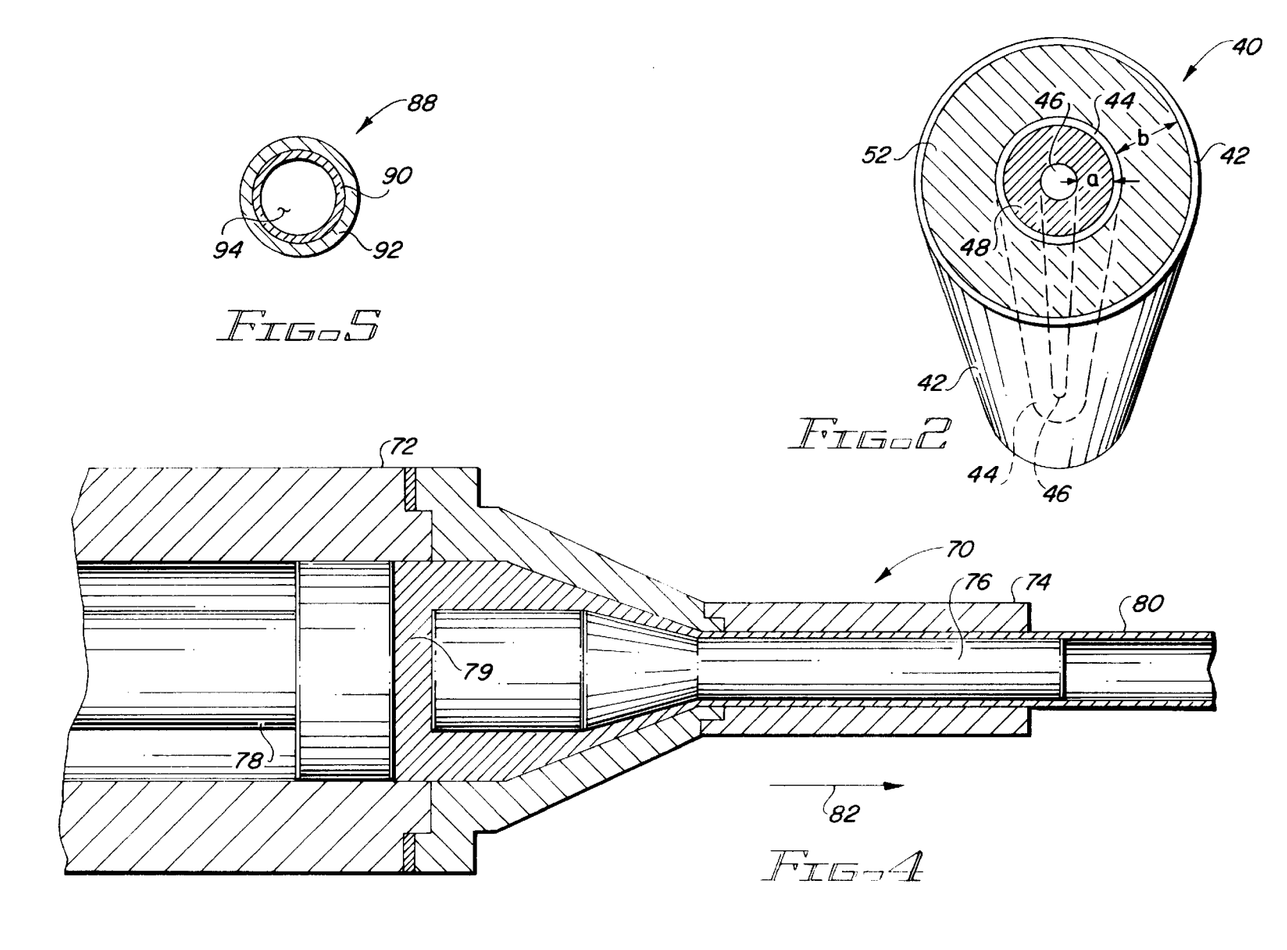
FIG. 2 is a perspective view of the divided preform barrel which is used to form a preform billet during the inventive process.
FIG. 4 is a diagrammatic cross-sectional view of a mandrel and die assembly which is used to extrude the carbon containing vascular graft during the inventive process.
FIG. 5 is a cross-sectional view of a intraluminal carbon lined vascular graft made in accordance with the inventive process.

Following compounding, both the polymeric compound and the carbon polymeric carbon compound are preformed into a compressed cylinder by undertaking a series of short steps. First, the polymeric carbon compound is poured 38 into the inner barrel of a divided performer by directing it through a funnel which is fit to the outside of the inner barrel. FIG. 2 illustrates the divided preform barrel 40 which is used in preforming the compounds into a compressed cylinder. The divided preform barrel 40 comprises an outer hollow cylindrical member 42, an inner hollow cylindrical member 44, and a central solid cylindrical member 46. The inner hollow cylindrical member 44 is concentrically contained within the 20 outer hollow cylindrical member 42.

The polymeric carbon compound is poured 38 within a first area 48 located between the inner hollow cylindrical member 44 and the central solid cylindrical member 46. The polymeric compound is then poured 50 within a second area 52 located between the outer hollow cylindrical member 42 and the inner hollow cylindrical member 44.

In a preferred embodiment, the outer hollow cylindrical member 42 has a radius greater than the radius of the inner hollow cylindrical member 44. The diameter of the components which comprise the preform barrel will vary depending on the size and type of vascular graft that is being produced. The preform barrel 40 that was used with the composition parameters set out in Example 1 had a radius of approximately two inches. The first area 48 between the inner hollow cylindrical member 44 and the central solid cylindrical member 46 had a radius of approximately two-sixteenths inches, the inner hollow cylindrical member 44 had a wall thickness of approximately one-sixteenth of an inch, and the second area 50 located between the outer hollow cylindrical member 42 and the inner hollow cylindrical member 44 had a radius of approximately nine-sixteenths inches.

The materials contained in the divided preform barrel 40, namely the polymeric compound and the polymeric carbon compound, are then compressed 54. The materials are compressed 54 by placing the divided preform barrel 40 on a press 56 such as that shown in FIG. 3. After compressing the materials contained within the divided preform barrel 40, the inner cylindrical member 44, the outer cylindrical member 42, and the center solid cylindrical member 46 of the divided preform barrel 40 are removed 57 to obtain a compressed cylinder of material 58. The inner hollow cylindrical member 44 is removed without disturbing the interface between the carbon polymeric compound and the polymeric compound.

The press 56 used during the compression 54 of the polymeric compound and the carbon polymeric compound is driven by a power drive 60 which forces a top member 62 toward a bottom member 64 to compress the material 58 within the divided preform barrel 40. Hollow cylindrical tubes 66 of varying thicknesses are used to compress the material 58 within the divided preform barrel 40 by slidably reciprocating around the inner hollow cylindrical member 44, the outer hollow cylindrical member 42, and the center solid cylindrical member 46 of the divided preform barrel 40.

Alternatively, the dividers within the preform barrel may be removed prior to compression, without disturbing the interface between the different compounds, and then compressed to form a billet for extrusion. The compressed cylinder of material, or billet, is co-extruded via a ram extruder assembly 70 such as that illustrated in FIG. 4. The ram extruder assembly 70 consists of an extrusion barrel 72, an extrusion die 74, a mandrel 76, and a ram 78.

The compressed cylinder of material is placed within the extrusion barrel 72. Force is applied to ram 78 which in turn expels pressure on the compressed cylinder of material. The pressure causes the compressed cylinder of material 79 to be extruded around mandrel 76, through extrusion die 74, and issue as a tubular extrudate 80. An arrow 82 shows the direction of the extrusion. The tubular extrudate 80 is then expanded 84 and sintered 86 (See FIG. 1) in accordance with the expansion and sintering procedures undertaken with pure PTFE vascular grafts which are well known in the art.

FIG. 5 illustrates a cross-section of the carbon-lined vascular graft 88. The inner luminal layer 90 of the vascular graft 88 is comprised of the previously described polymeric carbon compound and the outer layer 92 of the vascular graft 88 is comprised of the previously described polymeric compound. The carbon contained in the polymeric carbon compound is now an integral part of the luminal wall of the vascular graft 88. Blood flowing through the lumen 94 of the vascular graft 88 is in direct contact with the polymeric carbon compound which results in a decreased incidence of thrombus formation on the luminal wall of the carbon lined vascular graft 88 over non-carbon lined vascular grafts. In addition, leaching of the carbon from the graft into the bloodstream is minimal compared to other carbon-lined grafts which are not co-extruded.

Physical tests were performed on three samples from three different lots that were processed according to the method depicted in FIG. 1.

The results of the physical tests were as follows:

| Lot Number | 1 | 2 | 3 |
|---|---|---|---|
| Inside Diameter (mm) | 4.0 | 5.0 | 6.0 |
|  | 4.0 | 5.0 | 6.0 |
|  | 4.0 | 5.0 | 6.0 |
| Wall Thickness (mm) | 0.498 | 0.468 | 0.440 |
|  | 0.542 | 0.475 | 0.474 |
|  | 0.486 | 0.481 | 0.468 |
| Water Entry Pressure (psi) | 3.8 | 3.4 | 3.4 |
|  | 4.2 | 3.6 | 3.4 |
|  | 4.2 | 3.8 | 3.6 |

Water Entry Pressure was defined as the pressure at which water passes from the inner wall to the outer wall of the graft. To determine the Water Entry Pressure of a given graft, the graft was filled with water and pressurized to an initial value. The pressure was then increased gradually until water was observed on the external surface of the graft. This pressure was recorded as the Water Entry Pressure.

All characteristics of the grafts were in the acceptable quality control range for non-carbon lined PTFE vascular grafts. It was further determined that the sifting of the carbon and the use of higher lube levels aids the dispersion of the carbon throughout the luminal layer of the graft.

EXAMPLE 2

The following amounts were used in compounding the polymeric carbon compound and the polymeric compound:

Polymeric carbon compound:

| PTFE resin | 460.5 grams |
|---|---|
| carbon (activated charcoal powder) | 40.7 grams |

The activated carbon had a particle size wherein 97% of the activated carbon passed through a 150 micron sieve.

Polymeric compound:

| PTFE resin | 500 grams |
|---|---|

The process outlined in FIG. 1 was again carried out with the above identified compositions. Physical tests were performed on both the 6.0 mm standard IMPRA vascular grafts and the carbon lined vascular grafts formed from the inventive process. PTFE resin batches and lubricant batches were controlled. The results were as follows:

|  | CARBON-LINED GRAFT | | STANDARD GRAFT | |
|---|---|---|---|---|
|  | Avg. | St. D. | Avg. | St. D. |
| Inside Diameter (mm) | 6.00 | 0.000 | 5.98 | 0.075 |
| Wall Thickness (mm) | 0.42 | 0.004 | 0.44 | 0.007 |
| Water Entry pressure (psi) | 5.84 | 0.080 | 5.60 | 0.782 |
| Suture Retention Strength (g) | 1241.50 | 104.500 | 1272.50 | 111.500 |

Suture Retention Strength was defined as the force necessary to pull a suture from the graft, or cause the wall of the graft to fail. The graft was cut normal to the long axis and a suture was inserted 2 millimeters (mm) from the end of the graft, through one wall of the graft, to form a half loop. The graft and suture were positioned on a tensile testing machine having a load cell and gripping equipment. The suture was then pulled at the rate of 150±50 mm per minute. The force required to pull the suture through the graft or cause the wall of the graft to fail was recorded as the suture retention strength. This force was recorded in grams.

All characteristics of the grafts were in the acceptable quality control range for standard PTFE vascular grafts. Only one characteristic showed a statistical significant difference between the carbon lined grafts and the standard grafts.

| T. TEST COMPARISON | |
|---|---|
| Wall Thickness | P value = 0.0003 |

Figure 6:
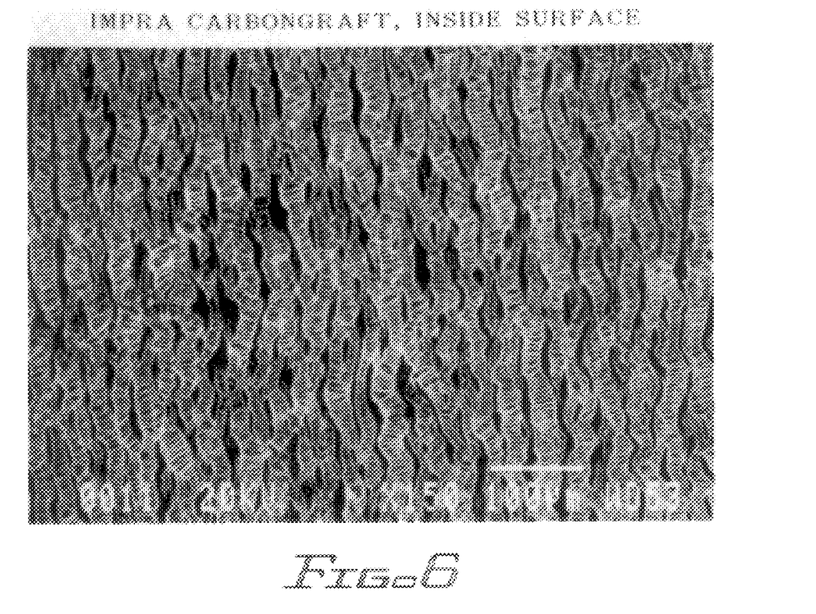
FIG. 6 is a scanning electron micrograph (SEM) of the inside surface of a carbon lined vascular graft made in accordance with the inventive process.
Figure 7:
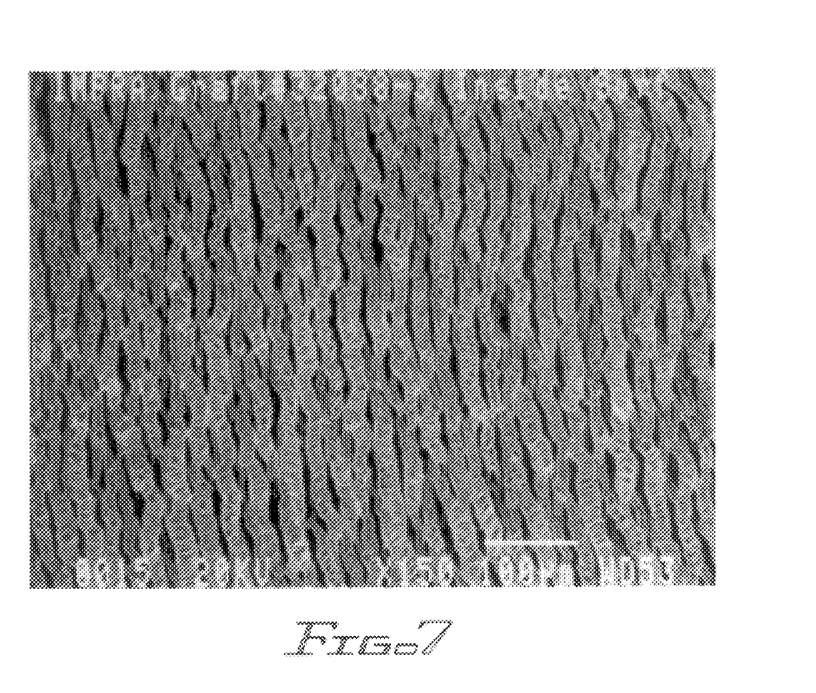
FIG. 7 is a SEM of the inside surface of a standard expanded polytetrafluoroethylene (ePTFE) vascular graft.
Figure 8:
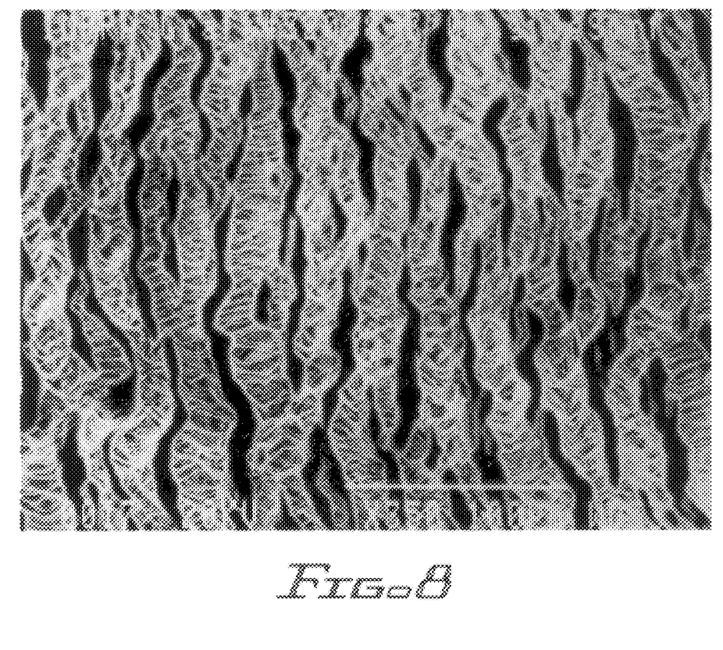
FIG. 8 is a SEM of the outside surface of a carbon lined vascular graft made in accordance with the inventive process.
Figure 9:
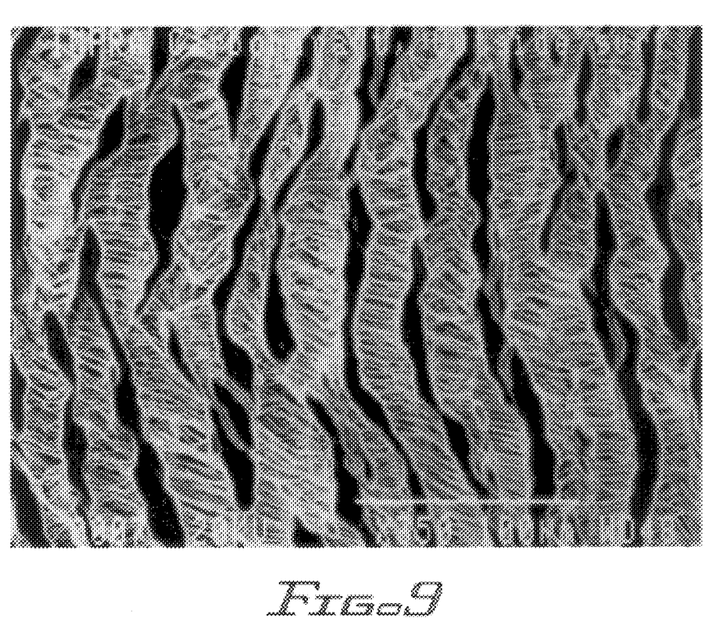
FIG. 9 is a SEM of the outside surface of a standard ePTFE vascular graft.

FIGS. 6 and 7 are scanning electron micrographs taken at 150× magnification of the inside surfaces of a carbon lined vascular graft and standard vascular graft, respectively, which were processed in accordance with Example 2 above. FIGS. 8 and 9 represent scanning electron micrographs taken at 350× magnification of the outside surfaces of the carbon lined vascular graft and the standard vascular graft, respectively. As can be seen from FIGS. 6–9, there are no visually discernable differences in the internodal distances in the scanning electron micrographs for the respective types of grafts.

Figure 10:
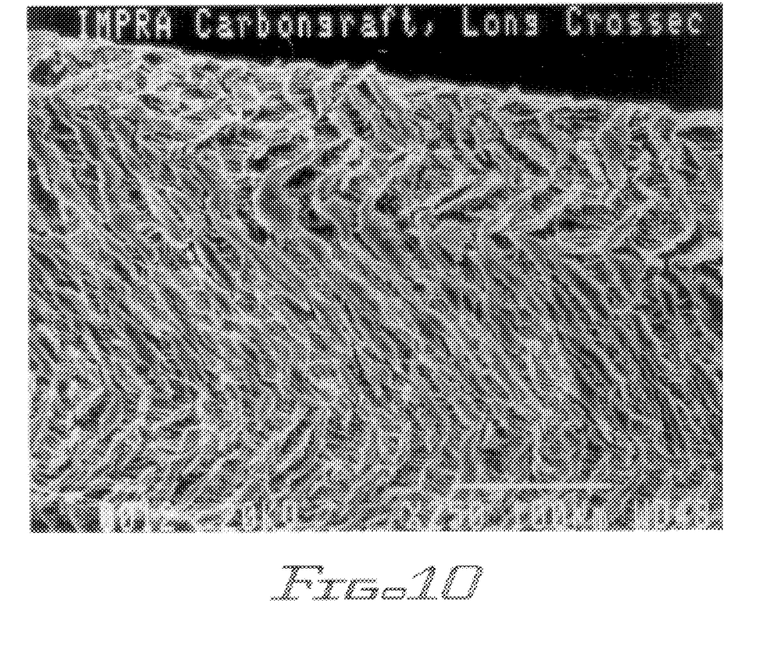
FIG. 10 is a SEM of a longitudinal cross section of a carbon lined vascular graft made in accordance with the inventive process taken at 250× magnification.
Figure 11:
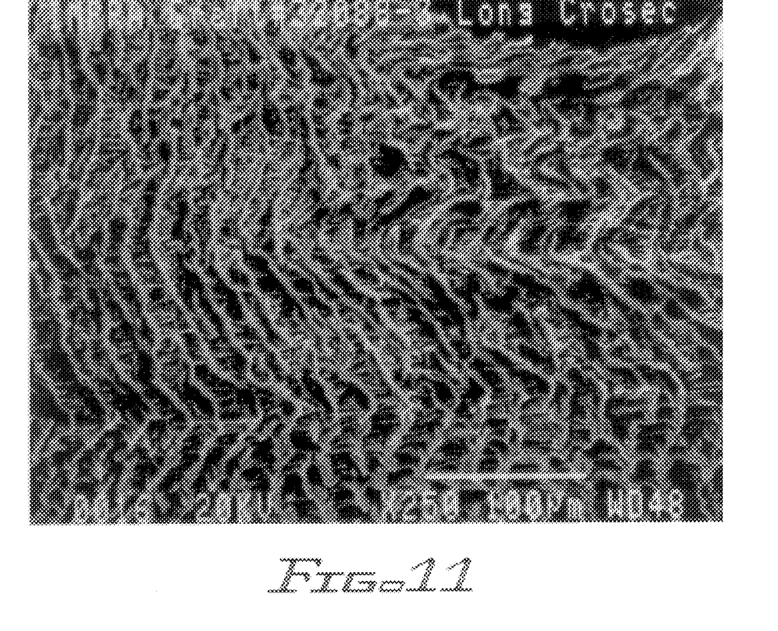
FIG. 11 is a SEM of a longitudinal cross section of a standard ePTFE vascular graft taken at 250× magnification.
Figure 12:
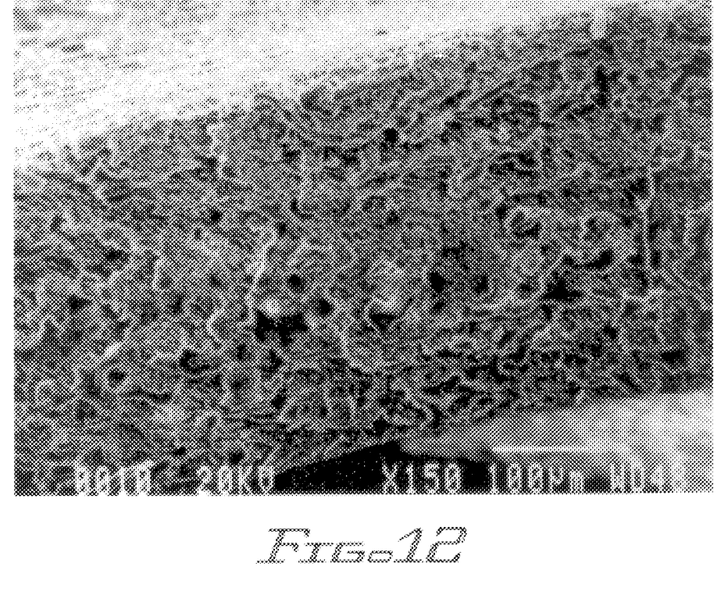
FIG. 12 is a SEM of a longitudinal cross section of a carbon lined vascular graft made in accordance with the inventive process taken at 150× magnification.
Figure 13:
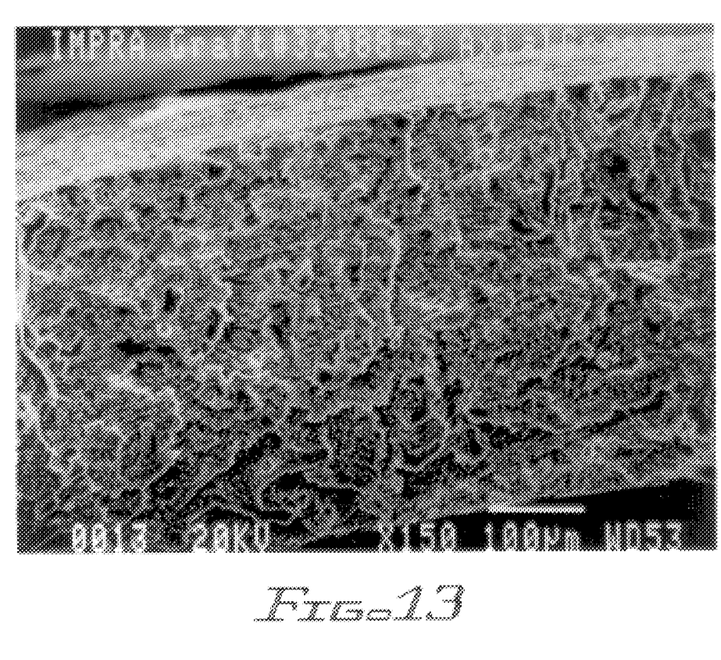
FIG. 13 is a SEM of a longitudinal cross section of a standard ePTFE vascular graft taken at 150× magnification.

FIGS. 10 and 11 represent scanning electron micrographs taken at 250× magnification of a longitudinal cross section of the carbon lined and standard vascular grafts shown in the previous four figures and processed in accordance with Example 2 above. FIGS. 12 and 13 show scanning electron micrographs taken at 150× magnification of a longitudinal cross-section of the carbon lined vascular graft and the standard graft, respectively. Again, no visually discernable differences were observed in the scanning electron micrographs of the graft cross-sections.

In contrast to the above examples, an exterior or outer carbon lined vascular graft may be produced using the process outlined in FIG. 1. However, instead of loading the polymeric carbon compound into the first area 48 of the divided preformer 40, the carbon polymeric compound is loaded into the second area 52 of the divided preformer 40. The dimensions of the cylindrical members 42, 44, 46 may change in order to produce a billet that can be extruded to form a vascular graft having a thin carbon lined exterior surface.

Further, a carbon containing vascular graft may be formed which comprises a carbon containing monolithic layer. The carbon containing graft can be formed from a single compound billet of compressed carbon polymeric compound which is extruded to form the monolithic graft. A carbon containing graft having carbon throughout the entire wall of the graft may also be formed by loading a carbon polymeric compound into both the inner and outer areas 48, 52 of the divided preformer 40 and continuing the remaining process outlined in FIG. 1. The carbon polymeric compounds loaded into both the inner and outer areas 48, 52 of the divided preformer 40 may or may not comprise the same % weight of the carbon component.

All of the previously described carbon containing vascular grafts may further comprise a bioactive substance which is capable of being time-released from the vascular grafts. The bioactive substance may include anticoagulants, anti-microbial agents, anti-inflammatories, growth factors, smooth muscle contraction inhibitors, antithrombotics, anti-platelet agents, non steroidal anti-inflammatory drugs, infectin, ticlopidene, or any other substance which enhances the utility or value of the graft for implant purposes.

The bioactive substance is incorporated into the carbon containing graft by methods known in the art. For example, the carbon containing vascular graft may be soaked in the desired bioactive substance, post sintering of the graft, and then dried. A negative or positive pressure may also be used to drive the bioactive substance into the pores of the vascular graft. Other methods for bonding a bioactive substance to the carbon containing graft are described in U.S. Pat. Nos. 4,229,838 and 4,749,585, and are herein incorporated by reference. As previously stated, the electronegative charge of the carbon component in the carbon containing vascular graft may facilitate in binding the bioactive substance to the vascular graft.

While a preferred form of the invention has been shown in the drawings and described, since variations in the preferred form will be apparent to those skilled in the art, the invention should not be construed as limited to the specific form shown and described, but instead is as set forth in the following claims.

I claim:

1. A tubular vascular graft, comprising an activated carbon and expanded polytetrafluoroethylene lumenal layer and an expanded polytetrafluoroethylene layer concentrically joined and co-extruded with one another to form an integral activated carbon and expanded polytetrafluoroethylene tubular wall structure wherein the activated carbon and expanded polytetrafluoroethylene lumenal layer further including a bioactive substance loaded therein fluid flow communication with a lumenal surface of the tubular wall structure.

2. The vascular graft of claim 1 wherein said bioactive substance comprises at least one of anticoagulant, an anti-microbial agent, an anti-inflammatory, a growth factor, a smooth muscle inhibitor, an antithrombotic, an antiplatelet agent, and a non-steroidal anti-inflammatory drug.

3. The tubular vascular graft according to claim 1, wherein the activated carbon has an average particle size less than or equal to 150 microns.

4. The tubular vascular graft according to claim 1, wherein the activated carbon further comprises an admixture of activated carbon and graphite.

5. A carbon containing vascular graft comprising:
   a first layer forming a lumenal surface of the carbon containing vascular graft and defining a flow passage therethrough, said first layer comprising an admixture of expanded polytetrafluoroethylene and activated carbon; and
   a second layer surrounding said first layer wherein said second layer comprises one of expanded polytetrafluoroethylene or an admixture of expanded polytetrafluoroethylene and activated carbon, wherein the first and second layers are concentrically and integrally joined to one another by:
   a) molding a preform billet having a solid inner cylindrical portion formed of an admixture of polytetrafluoroethylene and activated carbon and an outer cylindrical portion surrounding said solid inner cylindrical portion and formed of at least one of polytetrafluoroethylene or an admixture of polytetrafluoroethylene and activated carbon;
   b) co-extruding the first and second layers within the preformed billet to form a carbon-containing tubular extrudate;
   c) longitudinally expanding the carbon-containing tubular extrudate to form a microporous polytetrafluoroethylene microstructure matrix consisting of nodes interconnected by fibrils with the activated carbon dispersed within the microporous polytetrafluoroethylene microstructure matrix; and
   d) sintering the longitudinally expanded carbon-containing tubular extrudate wherein at least one of said first and second layers further comprises at least one bioactive compound selected from the group consisting of anticoagulant, anti-microbial agent anti-inflammatory, growth factor, smooth muscle inhibitor, antithrombotic, antiplatelet agent, and non-steroidal anti-inflammatory.

6. The carbon containing vascular graft of claim 5 wherein the step of molding a preform billet further comprises the steps of:
   a) providing a preform barrel which is divided into inner and outer hollow concentric cylindrical sections by a hollow cylindrical divider;
   b) compounding a polytetrafluoroethylene-lubricant admixture;
   c) pouring the compounded polytetrafluoroethylene-lubricant admixture into one of the inner and outer cylindrical sections of the preform barrel;

d) compounding a polytetrafluoroethylene-lubricant-activated carbon admixture to form a polymeric carbon compound;

e) pouring the polymeric carbon compound into a second one of the inner and outer cylindrical sections of the preform barrel;

f) pressing said preform barrel to compact the polymer compound and the polymeric carbon compound; and g) removing said preform barrel.

7. The carbon lined vascular graft of claim 6 wherein the activated carbon is present at approximately 3% to 20% by weight of the polytetrafluoroethylene.

8. The carbon lined vascular graft of claim 6 wherein said carbon component is an activated charcoal powder.

9. The carbon containing vascular graft according to claim 5, wherein the activated carbon has an average particle size less than or equal to 150 microns.

10. The carbon containing vascular graft according to claim 5, wherein the activated carbon further comprises an admixture of activated carbon and graphite.

11. A carbon containing vascular graft comprising:

a first layer forming a lumenal surface of the carbon containing vascular graft and defining a flow passage therethrough, said first layer comprising an admixture of expanded polytetrafluoroethylene and activated carbon; and a second layer surrounding said first layer wherein said second layer comprises one of expanded polytetrafluoroethylene or an admixture of expanded polytetrafluoroethylene and activated carbon, wherein the first and second layers are concentrically and integrally joined to one another by:

a) molding a preform billet having a solid inner cylindrical portion formed of an admixture of polytetrafluoroethylene and activated carbon and an outer cylindrical portion surrounding said solid inner cylindrical portion and formed of at least one of polytetrafluoroethylene or an admixture of polytetrafluoroethylene and activated carbon, said step of molding a preform billet comprising the steps of:

i. providing a preform barrel which is divided into inner and outer hollow concentric cylindrical sections by a hollow cylindrical divider;

ii. compounding a polytetrafluoroethylene-lubricant admixture;

iii. pouring the compounded polytetrafluoroethylene-lubricant admixture into one of the inner and outer cylindrical sections of the preform barrel;

iv. compounding a polytetrafluoroethylene-lubricant-activated carbon admixture to form a polymeric carbon compound;

v. pouring the polymeric carbon compound into a second one of the inner and outer cylindrical sections of the preform barrel;

vi. pressing said preform barrel to compact the polymer compound and the polymeric carbon compound; and vii. removing said preform barrel;

b) co-extruding the first and second layers within the preformed billet to form a carbon-containing tubular extrudate;

c) longitudinally expanding the carbon-containing tubular extrudate to form a microporous polytetrafluoroethylene microstructure matrix consisting of nodes interconnected by fibrils with the activated carbon dispersed within the microporous polytetrafluoroethylene microstructure matrix;

d) sintering the longitudinally expanded carbon-containing tubular extrudate; and e incorporating a bioactive substance into the activated carbon prior to admixing the polytetrafluoroethylene-activated carbon-lubricant admixture.

12. The carbon lined vascular graft of claim 11 wherein the bioactive substance comprises at least one of an anticoagulant, an anti-microbial agent, an anti-inflammatory, a growth factor, a smooth muscle inhibitor, an antithrombotic, an antiplatelet agent, and a non-steroidal anti-inflammatory drug.

13. A carbon containing vascular graft comprising:

a first layer forming a lumenal surface of the tubular member and defining a flow passage therethrough, said first layer comprising an admixture of expanded polytetrafluoroethylene and activated carbon; and a second layer surrounding said first layer wherein said second layer comprises one of expanded polytetrafluoroethylene or an admixture of expanded polytetrafluoroethylene and activated carbon, wherein the first and second layers are concentrically and integrally joined to one another by:

a) molding a preform billet having an inner cylindrical portion formed of an admixture of polytetrafluoroethylene and activated carbon and an outer cylindrical portion surrounding the inner cylindrical portion and formed of at least one of polytetrafluoroethylene or an admixture of polytetrafluoroethylene and activated carbon;

b) co-extruding the first and second layers within the preformed billet to form a carbon-containing tubular extrudate;

c) longitudinally expanding the carbon-containing tubular extrudate to form a microporous polytetrafluoroethylene microstructure matrix consisting of nodes interconnected by fibrils with the activated carbon dispersed within the microporous polytetrafluoroethylene microstructure matrix; and d) sintering the longitudinally expanded carbon-containing tubular extrudate.

14. The carbon containing vascular graft of claim 13 wherein the step of molding a preform billet further comprises the steps of:

a) providing a preform barrel which is divided into inner and outer hollow concentric cylindrical sections by a hollow cylindrical divider;

b) compounding a polytetrafluoroethylene-lubricant admixture;

c) pouring the compounded polytetrafluoroethylene-lubricant admixture into one of the inner and outer cylindrical sections of the preform barrel;

d) compounding a polytetrafluoroethylene-lubricant-activated carbon admixture to form a polymeric carbon compound;

e) pouring the polymeric carbon compound into a second one of the inner and outer cylindrical sections of the preform barrel;

f) pressing said preform barrel to compact the polymer compound and the polymeric carbon compound; and g) removing said preform barrel.

15. The carbon lined vascular graft of claim 13 wherein the activated carbon is present at approximately 3% to 20% by weight of the polytetrafluoroethylene.

16. The carbon lined vascular graft of claim 13 wherein the activated carbon is an activated charcoal powder.

* * * * *